(12) United States Patent
Antane et al.

(10) Patent No.: US 6,288,099 B1
(45) Date of Patent: *Sep. 11, 2001

(54) SUBSTITUTED BENZOFURANOINDOLES AND INDENOINDOLES AS NOVEL POTASSIUM CHANNEL OPENERS

(75) Inventors: Schuyler A. Antane, West Windsor; John A. Butera, Clarksburg, both of NJ (US); Joseph R. Lennox, Morrisville, NC (US)

(73) Assignee: American Home Products Corporation, Madison, NJ (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/454,030

(22) Filed: Dec. 3, 1999

Related U.S. Application Data

(60) Provisional application No. 60/135,110, filed on Dec. 4, 1998, now abandoned.

(51) Int. Cl.$^7$ .................... A61K 31/41; A61K 31/407; C07D 487/04
(52) U.S. Cl. ............ 514/382; 514/383; 514/410; 548/252; 548/266.4; 548/421
(58) Field of Search ................ 548/421, 252, 548/266.4; 514/410, 382, 383

(56) References Cited

U.S. PATENT DOCUMENTS 5,612,356  3/1997  Yoshimura et al. ........... 514/338

FOREIGN PATENT DOCUMENTS

| 0447703 | 3/1990 | (EP) . |
| 0404536 | 6/1990 | (EP) . |
| 0409410 | 6/1990 | (EP) . |
| 06228554 | 8/1994 | (JP) . |
| 9015799 | 12/1990 | (WO) . |
| 9015800 | 12/1990 | (WO) . |
| 9114688 | 10/1991 | (WO) . |
| 9414777 | 1/1998 | (WO) . |

OTHER PUBLICATIONS

Bair, CA 116:235614, 1992.*
J. Primeau et al., Current Pharmaceutical Design, I, 391–406, (1995).
Edwards et al., Exp. Opin. Invest. Drugs (1996), 5(11):1453–1464.
Gopalakrishnan et al., Drug Dev. Research, 28:95–127 (1993).
Atwal, Medical Research Reviews, vol. 12, No. 6, 569–591 (1992).
Adamczyk et al., J. Org. Chem., (1984) 49, 4226–4237.
Graupner et al., Tetrahedron Lett., vol. 36, No. 32, pp. 5827–5830, (1995).
Brown et al., Tetrahedron, vol. 49, No. 39, pp. 8919–8932, (1993).
Brown et al., Tetrahedron, vol. 47, No. 25, pp. 4383–4408, (1991).
Cagniant, P. et al., Hebd. Seances Acad. Sci. C, (1976)282(21), 993–6.
Ellingboe, J. et al., J. Med. Chem., (1992), 35(7), 1176–1183.
Kim et al., J. of Med. Chem., (1993), vol. 36, No. 16 pp. 2335–2342.
Brown et al., Tetrahedron Lett., vol. 32, No. 6, pp. 801–802, (1991).
Shertzer H.G., Fd. Chem. Tox. (1991), 29(6) 391–400.
Smith et al., Org. Prep. and Procedures Int., 10(3), 123–131 (1978).
Hojo et al., J. Amer. Chem. Soc., 91, 5170 (1969).
Bundgaard et al., International J. of Pharmaceutics, 55, (1989) 91–97.
Aono et al., Chem. Pharm. Bull., 26(4) 1153–1161 (1978).
Tobias, P. et al., J. Amer. Chem. Soc., (1969) 91 (18), 5171–5173.

* cited by examiner

Primary Examiner—Laura L. Stockton
(74) Attorney, Agent, or Firm—Daniel B. Moran

(57) ABSTRACT

Compounds of the Formulae (I) and (II):

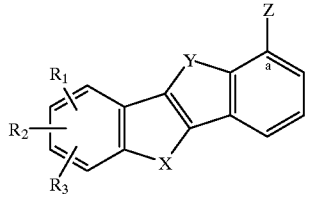

(I) and (II)

wherein $R_1$, $R_2$, $R_3$, X, Y and Z are as defined in the specification which compounds are useful in the treatment of disorders associated with smooth muscle contraction via potassium channel modulation.

19 Claims, No Drawings

SUBSTITUTED BENZOFURANOINDOLES AND INDENOINDOLES AS NOVEL POTASSIUM CHANNEL OPENERS

CROSS REFERENCE TO RELATED APPLICATIONS

This application claims benefit of U.S. Provisional Application No. 60/135,110 now abandoned, which was converted from U.S. patent application Ser. No.09/205,770, filed Dec. 4, 1998 Pursuant to a petition filed under 37 C.F.R. 1.53 (c) (2) filed Feb. 16, 1999.

BACKGROUND OF INVENTION

1. Field of the Invention

The present invention relates to a series of substituted tetracyclic heteroaromatic benzofuranoindoles and indenoindoles having pharmacological activity, to a process for their preparation, to pharmaceutical compositions containing them, and to their use in the treatment of disorders associated with smooth muscle contraction, via potassium channel modulation. Such disorders include, but are not limited to: urinary incontinence, asthma, premature labor, irritable bowel syndrome, congestive heart failure, angina, and cerebral vascular disease.

2. Description of the Prior Art

Modulation of potassium channels remains at the forefront of current approaches for controlling resting cell membrane potential and affecting cell excitability. A wide variety of discrete potassium channels exist and these have been thoroughly classified according to structure, function, pharmacological properties, and gating mechanisms in several recent reviews [Rudy, B. *Neuroscience* 1988, 25, 729–749; Atwal, K., *Medicinal Research Reviews* 1992, 12, 569–591; Gopalakrishnan, M. et al., *Drug Development Research* 1993, 28, 95–127; Primeau, J. et al. *Current Pharmaceutical Design* 1995, 1, 391–406; Edwards, G. et al. *Exp. Opin. Invest. Drugs* 1996, 5 (11), 1453–1464]. Activation of these channels augments transmembrane $K^+$ flux, thus effecting hyperpolarization of the cell membrane towards the Nernst $K^+$ equilibrium potential (−90 mV), and subsequent closure of the voltage-gated $Ca^{2+}$ channels. As a result, the hyperactive cell becomes less excitable and therefore less prone to further stimulation; thus leading to relaxation in the case of smooth muscle. As a result of this pharmacologic action, therapeutic potential for potassium channel activators in cardiovascular disorders, metabolic disorders, central nervous system disorders, bronchial asthma, and irritable bladder is being vastly explored.

A series of heterotetracyclic methylamnino benzofuranoindoles compounds are reported by Bair, K. W., in WO 91/14688 and EP-447703-A1 and are useful as antitumor and biocidal agents.

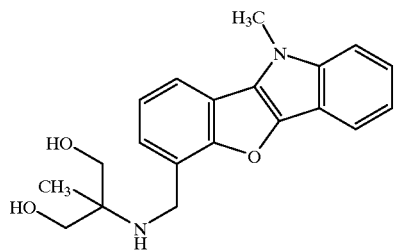

An example disclosed is 2-methyl-2-(((10-methyl-H-benzofuro(3,2-b)indol-6-yl)methyl)amino)-1,3-propanediol.

A series of indenoindoles claimed as useful medicinal antioxidants and free-radical scavengers are disclosed by Sainsbury et al. in EP-404536-A1.

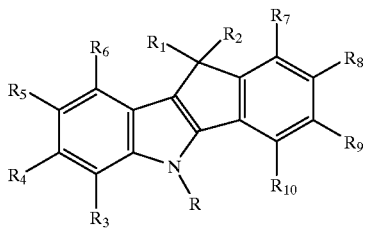

A series of indenoindoles useful as a component in an organic electroluminescent element are disclosed in JP-06-228554.

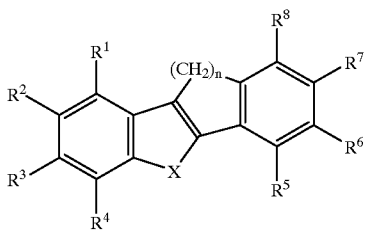

X is —O—, —S, -, $SO_2$-, or —$NR^9$

A related series of tetrahydro indeno-indole analogs is disclosed by Sainsbury, M. in WO 90/15799 and in EP-409410-B1.

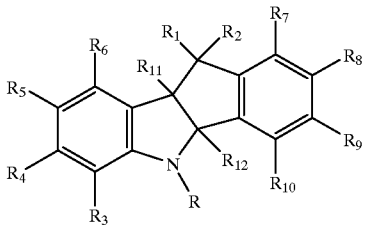

These compounds are also claimed as useful antioxidants for the treatment of atherosclerosis, thrombosis, embolism and Parkinson's disease.

The synthesis and antioxidant properties of a series of indeno-indoles and indolines are reported in several papers [Brown, D. W. et al., *Tetrahedron* 1991, 47 (25), 4383–4408; Brown, D. W. et al., *Tetrahedron* 1993, 49 (39), 8919–8932; Graupner, P. R. et al., *Tetrahedron Lett.* 1995, 36 (32) 5827–5830; Shertzer, H. G. et al., *Fd. Chem. Tox.* 1991, 29 (6) 391–400]. Reported also by Brown, F. C. et al., *Tetrahedron Lett.* 1991, 32 (6) 801–802 are flash-vacuum pyrolysis methods for the synthesis of substituted indeno[1,2-b] indoles.

The present invention differs from the prior art by requiring the Z substituent, defined below as a carboxylic acid moiety, a bioisosteric equivalent of a carboxylic acid, or a derivative thereof to be substituted at position a of the tetracyclic heteroaromatic benzofuranoindoles and indenoindoles of Formulae (I) and (II). The compounds of this invention have reported potassium channel activation and the resulting smooth muscle relaxing properties are uniquely tissue-selective for bladder tissue.

SUMMARY OF THE INVENTION

Accordingly, the present invention discloses compounds represented by Formula (I):

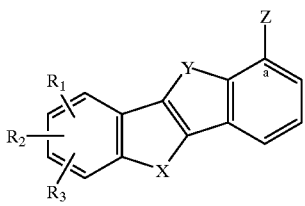

(I)

wherein:
R$_1$, R$_2$ and R$_3$ are, independently, hydrogen, halogen, nitro, cyano, alkyl of 1 to 10 carbon atoms, cycloalkyl of 3 to 10 carbon atoms, alkoxy of 1 to 10 carbon atoms (optionally substituted with halogen), amino, alkylamino of 1 to 10 carbon atoms, —SO$_3$H, —SO$_2$NH$_2$, —NHSO$_2$R$_{14}$,

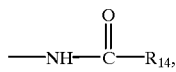

R$_{15}$SO$_2$-, carboxyl and aryl of 6 to 12 carbon atoms, or an acyl substituent selected from formyl, alkanoyl of 2 to 7 carbon atoms, alkenoyl of 3 to 7 carbon atoms, alkylsulfonyl of 1 to 7 carbon atoms, aroyl of 7 to 12 carbon atoms, arylalkenoyl of 9 to 20 carbon atoms, arylsulfonyl of 6 to 12 carbon atoms, arylalkanoyl of 8 to 12 carbon atoms or arylalkylsulfonyl of 7 to 12 carbon atoms;

Y is —O— and-NR$_4$;
X is —O—, when Y is —NR$_4$;
X is —NR$_4$, when Y is —O—;
R$_4$ is hydrogen, alkyl of 1 to 10 carbon atoms, cycloalkyl of 3 to 10 carbon atoms, aryl of 6 to 12 carbon atoms, or an acyl substituent selected from formyl, alkanoyl of 2 to 7 carbon atoms, alkenoyl of 3 to 7 carbon atoms, alkylsulfonyl of 1 to 7 carbon atoms, aroyl of 7 to 12 carbon atoms, arylalkenoyl of 9 to 20 carbon atoms, arylsulfonyl of 6 to 12 carbon atoms, arylalkanoyl of 8 to 12 carbon atoms and arylalkylsulfonyl of 7 to 12 carbon atoms;
R$_5$ and R$_6$ are independently hydrogen, alkyl of 1 to 10 carbon atoms, cycloalkyl of 3 to 10 carbon atoms, aryl of 6 to 12 carbon atoms, or fluorine;
Z substituted at position a is selected from the group consisting of

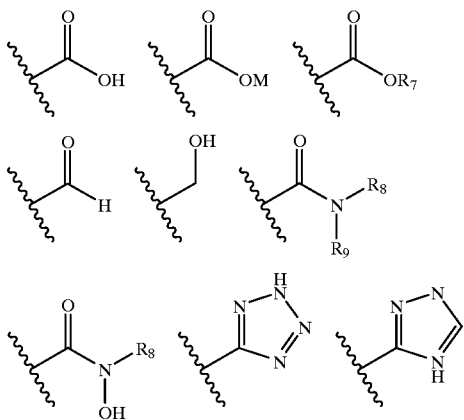

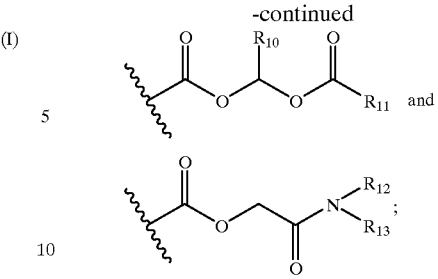

M is an alkali metal cation or an alkaline earth metal cation;
R$_7$ is alkyl of 1 to 10 carbon atoms, cycloalkyl of 3 to 10 carbon atoms, aralkyl of 7 to 20 carbon atoms, or aryl of 6 to 12 carbon atoms;
R$_8$ and R$_9$ are, independently, hydrogen, alkyl of 1 to 10 carbon atoms, cycloalkyl of 3 to 10 carbon atoms, aralkyl of 7 to 20 carbon atoms, or aryl of 6 to 12 carbon atoms;
R$_{10}$, R$_{11}$, R$_{12}$ and R$_{13}$ are independently, alkyl of 1 to 10 carbon atoms;
R$_{14}$ is a straight chain alkyl of 1 to 10 carbon atoms;
R$_{15}$ is a straight chain alkyl of 1 to 10 carbon atoms (optionally substituted with halogen);
aroyl is benzoyl and naphthoyl which is optionally substituted with one to three substituents each independently selected from the group halogen, cyano, alkyl of 1 to 10 carbon atoms, alkoxy of 1 to 10 carbon atoms, —CF$_3$, and phenyl;
aryl is naphthyl, phenyl or phenyl optionally substituted with one to three substituents each independently selected from the group halogen, carboxy, alkyl of 1 to 10 carbon atoms, nitro, amino, alkoxy of 1 to 10 carbon atoms, and alkylamnino of 1 to 10 carbon atoms;
provided that R$_1$, R$_2$ and R$_3$ are not hydrogen when Z is —CHO, Y is —O— and X is —N—CH$_3$;
or a pharmaceutically acceptable salt thereof.

A preferred aspect of this invention includes compounds of Formula (I) including pharmaceutically acceptable salts thereof are those in the subgroup below, wherein the other variables of Formula (I) in the subgroups are as defined above wherein:
a) Y is —NR$_4$ when X is —O—;
More preferred aspects of this invention includes compounds of Formula (I) including pharmaceutically acceptable salts thereof are those in the subgroups below, wherein the other variables of Formula (I) in the subgroups are as defined above wherein:
Z is —CO$_2$H;
R$_1$ is halogen or nitro;
a) X is —O—, when Y is —NR$_4$; and
b) X is —NR$_4$, when Y is —O—;
Specifically preferred compounds of this invention according to general Formula (I) are the following compounds or a pharmaceutically acceptable salt thereof:
8-Bromo-10H-benzo[4,5]furo[3,2-b]indole-1-carboxylic acid;
8-Iodo-10H-benzo[4,5]furo[3,2-b]indole-1-carboxylic acid;
8-Chloro-10H-benzo[4,5]furo[3,2-b]indole-1-carboxylic acid;
8-Nitro-10H-benzo[4,5]furo[3,2-b]indole-1-carboxylic acid dihydrate;
8-Bromo-10H-benzo[4,5]furo[3,2-b]indole-1-carboxylic acid amide;
8-Bromo-10H-benzo[4,5]furo[3,2-b]indole-1-carboxylic acid methyl ester;
(8-Bromo-10H-benzo[4,5]furo[3,2-b]indol-1-yl)-methanol;

8-Bromo-10H-benzo[4,5]furo[3,2-b]indole-1-carboxylic acid hydroxy-methyl amide;
8-Bromo-10H-benzo[4,5]furo[3,2-b]indole-1-carbaldehyde;
8-Bromo-10H-benzo[4,5]furo[3,2-b]indole-1-carbonitrile hydrate;
8-Bromo-1-(1H-tetrazol-5-yl)-10H-benzo[4,5]furo[3,2-b]indole;
8-Bromo-10H-benzo[4,5]furo[3,2-b]indole-1-carboxylic acid (1,2,2-trimethyl-propyl)-amide;
8-Bromo-10H-benzo[4,5]furo[3,2-b]indole-1-carboxylic acid (1,1-dimethyl-propyl)-amide;
8-Bromo-10H-benzo[4,5]furo[3,2-b]indole-1-carboxylic acid methylamide;
8-Bromo-10-methyl-10H-benzo[4,5]furo[3,2-b]indole-1-carboxylic acid methyl ester; and
10H-Benzo[4,5]furo[3,2-b]indole-1-carboxylic acid.

In particular, this invention also provides a method of treating or inhibiting disorders associated with smooth muscle contraction, via potassium channel modulation in warm-blooded animals in need thereof, which comprises administering to said warm-blooded animals preferably mammals, most preferably humans an effective amount of a compound of general Formula (II) or a pharmaceutically acceptable salt thereof:

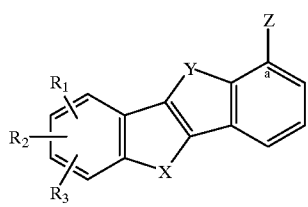
(II)

wherein:
$R_1$, $R_2$ and $R_3$ are, independently, hydrogen, halogen, nitro, cyano, alkyl of 1 to 10 carbon atoms, cycloalkyl of 3 to 10 carbon atoms, alkoxy of 1 to 10 carbon atoms (optionally substituted with halogen), amino, alkylamino of 1 to 10 carbon atoms, —$SO_3H$, —$SO_2NH_2$, —$NHSO_2R_{14}$,

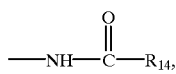

$R_{15}SO_2$-, carboxyl and aryl of 6 to 12 carbon atoms, or an acyl substituent selected from formyl, alkanoyl of 2 to 7 carbon atoms, alkenoyl of 3 to 7 carbon atoms, alkylsulfonyl of 1 to 7 carbon atoms, aroyl of 7 to 12 carbon atoms, arylalkenoyl of 9 to 20 carbon atoms, arylsulfonyl of 6 to 12 carbon atoms, arylalkanoyl of 8 to 12 carbon atoms or arylalkylsulfonyl of 7 to 12 carbon atoms;
Y is —$NR_4$ and —$CR_5R_6$;
X is —O—, when Y is —$NR_4$;
X is —$NR_4$, when Y is —$CR_5R_6$;
X is —$CR_5R_6$, when Y is —$NR_4$;
$R_4$ is hydrogen, alkyl of 1 to 10 carbon atoms, cycloalkyl of 3 to 10 carbon atoms, aryl of 6 to 12 carbon atoms, or an acyl substituent selected from formyl, alkanoyl of 2 to 7 carbon atoms, alkenoyl of 3 to 7 carbon atoms, alkylsulfonyl of 1 to 7 carbon atoms, aroyl of 7 to 12 carbon atoms, arylalkenoyl of 9 to 20 carbon atoms, arylsulfonyl of 6 to 12 carbon atoms, arylalkanoyl of 8 to 12 carbon atoms and arylalkylsulfonyl of 7 to 12 carbon atoms;

$R_5$ and $R_6$ are independently hydrogen, alkyl of 1 to 10 carbon atoms, cycloalkyl of 3 to 10 carbon atoms, aryl of 6 to 12 carbon atoms, or fluorine;
Z substituted at position a is selected from the group consisting of

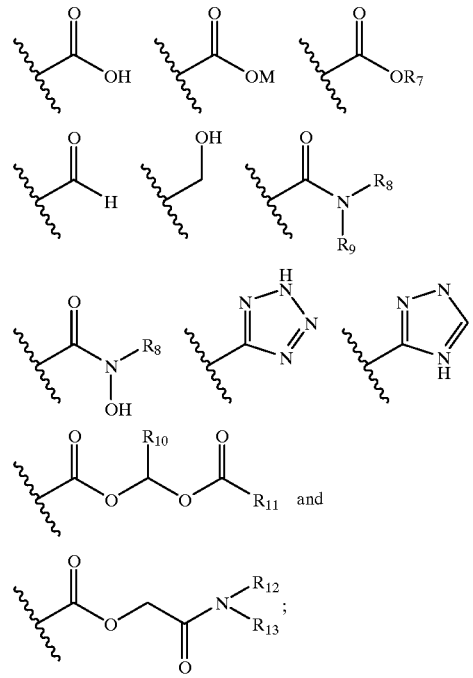

M is an alkali metal cation or an alkaline earth metal cation;
$R_7$ is alkyl of 1 to 10 carbon atoms, cycloalkyl of 3 to 10 carbon atoms, aralkyl of 7 to 20 carbon atoms, or aryl of 6 to 12 carbon atoms;
$R_8$ and $R_9$ are, independently, hydrogen, alkyl of 1 to 10 carbon atoms, cycloalkyl of 3 to 10 carbon atoms, aralkyl of 7 to 20 carbon atoms, or aryl of 6 to 12 carbon atoms;
$R_{10}$, $R_{11}$, $R_{12}$ and $R_{13}$ are independently, alkyl of 1 to 10 carbon atoms;
$R_{14}$ is a straight chain alkyl of 1 to 10 carbon atoms;
$R_{15}$ is a straight chain alkyl of 1 to 10 carbon atoms (optionally substituted with halogen);
aroyl is benzoyl and naphthoyl which is optionally substituted with one to three substituents each independently selected from the group halogen, cyano, alkyl of 1 to 10 carbon atoms, alkoxy of 1 to 10 carbon atoms, —$CF_3$, and phenyl;
aryl is naphthyl, phenyl or phenyl optionally substituted with one to three substituents each independently selected from the group halogen, carboxy, alkyl of 1 to 10 carbon atoms, nitro, amino, alkoxy of 1 to 10 carbon atoms, and alkylamino of 1 to 10 carbon atoms;
or a pharmaceutically acceptable salt thereof.

A preferred aspect of this invention includes compounds of Formula (II) including pharmaceutically acceptable salts thereof for use as a method of treating or inhibiting disorders associated with smooth muscle contraction, via potassium channel modulation in warm-blooded animals preferably mammals, most preferably humans in need thereof are those in the subgroups below, wherein the other variables of Formula (II) in the subgroups are as defined above wherein:
a) X is —O—, when Y is —$NR_4$;
b) X is —$NR_4$, when Y is —$CR_5R_6$; and
c) X is —$CR_5R_6$, when Y is —$NR_4$.

More preferred aspects of this invention includes compounds of Formula (II) including pharmaceutically acceptable salts thereof for use as a method of treating or inhibiting disorders associated with smooth muscle contraction, via potassium channel modulation in warm-blooded animals preferably mammals, most preferably humans in need thereof are those in the subgroups below, wherein the other variables of Formula (II) in the subgroups are as defined above wherein:

Z is —$CO_2H$;

$R_1$ is halogen or nitro;

a) X is —O—, when Y is —$NR_4$;
b) X is —$NR_4$, when Y is —$CR_5R_6$; and
c) X is —$CR_5R_6$, when Y is —$NR_4$.

Specifically preferred compounds of this invention according to general Formula (II) for use as a method of treating or inhibiting disorders associated with smooth muscle contraction, via potassium channel modulation in warm-blooded animals preferably mammals, most preferably humans in need thereof are the following compounds or a pharmaceutically acceptable salt thereof:

8-Bromo-10H-benzo[4,5]furo[3,2-b]indole-1-carboxylic acid;
8-Iodo-10H-benzo[4,5]furo[3,2-b]indole-1-carboxylic acid;
8-Chloro-10H-benzo[4,5]furo[3,2-b]indole-1-carboxylic acid;
8-Nitro-10H-benzo[4,5]furo[3,2-b]indole-1-carboxylic acid dihydrate;
8-Bromo-10H-benzo[4,5]furo[3,2-b]indole-1-carboxylic acid amide;
8-Bromo-10H-benzo[4,5]furo[3,2-b]indole-1-carboxylic acid methyl ester;
(8-Bromo-10H-benzo[4,5]furo[3,2-b]indol-1-yl)-methanol;
8-Bromo-10H-benzo[4,5]furo[3,2-b]indole-1-carboxylic acid hydroxy-methyl amide;
8-Bromo-10H-benzo[4,5furo[3,2-b]indole-1-carbaldehyde;
8-Bromo-10H-benzo[4,5]furo[3,2-b]indole-1-carbonitrile hydrate;
8-Bromo-1-(1H-tetrazol-5-yl)-10H-benzo[4,5]furo[3,2-b] indole;
8-Bromo-10H-benzo[4,5]furo[3,2-b]indole-1-carboxylic acid (1,2,2-trimethyl-propyl)-amide;
8-Bromo-10H-benzo[4,5]furo[3,2-b]indole-1-carboxylic acid (1,1- dimethyl-propyl)-amide;
8-Bromo-10H-benzo[4,5]furo[3,2-b]indole-1-carboxylic acid methylamide;
8-Bromo-10-methyl-10H-benzo[4,5]furo[3,2-b]indole-1-carboxylic acid methyl ester;
10H-Benzo[4,5]furo[3,2-b]indole-1-carboxylic acid;
8-Iodo-5,10-dihydro-indeno[1,2-b]indole-1-carboxylic acid 0.6 hydrate;
8-Sulfamoyl-5,10-dihydro-indeno[1,2-b]indole-1-carboxylic acid hemihydrate;
8-Fluoro-5,10-dihydro-indeno[1,2-b]indole-1-carboxylic acid;
8-Chloro-5,10-dihydro-indeno[1,2-b]indole-1-carboxylic acid;
8-Trifluoromethoxy-5,10-dihydro-indeno[1,2-b]indole-1-carboxylic acid;
8-Chloro-5,10-dihydro-indeno[1,2-b]indole-1-carboxylic acid ethyl ester;
8-Bromo-5,10-dihydro-indeno[1,2-b]indole-1-carboxylic acid ethyl ester;
10,10-Dimethyl-3-nitro-5,10-dihydro-indeno[1,2-b]indole-6-carboxylic acid;
8-Bromo-5,10-dihydro-indeno[1,2-b]indole-1-carboxylic acid; and
3-Bromo-5,10-dihydro-indeno[1,2-b]indole-6-carboxylic acid.

It is understood that the definition of compounds of Formulae (I) and (II), when $R_1$, $R_2$, $R_3$, $R_4$, $R_5$, $R_6$, $R_7$, $R_8$, $R_9$, $R_{10}$, $R_{11}$, $R_{12}$, $R_{13}$ or $R_{15}$ contain asymmetric carbons, encompass all possible stereoisomers and mixtures thereof which possess the activity discussed below. In particular, the definition encompasses racemic modifications and any optical isomers which possess the indicated activity. Optical isomers may be obtained in pure form by standard separation techniques or enantiomer specific synthesis. It is understood that this invention encompasses all crystalline forms of compounds of Formulae (I) and (II). The pharmaceutically acceptable salts of the basic compounds of this invention are those derived from such organic and inorganic acids as: lactic, citric, acetic, tartaric, fumaric, succinic, maleic, malonic, hydrochloric, hydrobromic, phosphoric, nitric, sulfuric, methanesulfonic, and similarly known acceptable acids. Where $R_1$, $R_2$, $R_3$, $R_4$, $R_5$, $R_6$, $R_7$, $R_8$, or $R_9$ contains a carboxyl group, or in the cases where Z is a carboxylic acid, salts of the compounds in this invention may be formed with bases such as alkali metals (Na, K, Li) or alkaline earth metals (Ca or Mg).

For the compounds of Formulae (I) and (II) defined above and referred to herein, unless otherwise noted, the following terms are defined:

Halogen, or halo as used herein means chloro, fluoro, bromo and iodo.

Alkyl as used herein means a branched or straight chain having from 1 to 10 carbon atoms and more preferably from 1 to 6 carbon atoms. Exemplary alkyl groups include methyl, ethyl, propyl, isopropyl, butyl, isobutyl, t-butyl, pentyl and hexyl.

Cycloalkyl as used herein means a saturated ring having from 3 to 10 carbon atoms and more preferably from 3 to 6 carbon atoms. Exemplary cycloalkyl rings include cyclopropyl, cyclobutyl, cyclopentyl and cyclohexyl.

Aryl as used herein means a homocyclic aromatic radical, whether or not fused, having 6 to 12 carbon atoms. Preferred aryl groups include phenyl, alpha-naphthyl and beta-naphthyl and the like optionally substituted with one to three substituents each independently selected from the group halogen, carboxy, alkyl of 1 to 10 carbon atoms, nitro, amino, alkoxy of 1 to 10 carbon atoms, and alkyl amino of 1 to 10 carbon atoms.

Aroyl as used herein refers to —C(O)aryl where aryl is as previously defined. Examples include benzoyl and naphthoyl which may optionally be substituted with one to three substituents each independently selected from the group halogen, cyano, alkyl of 1 to 10 carbon atoms, alkoxy of 1 to 10 carbon atoms, —$CF_3$ and phenyl.

Aralkyl as used herein means an aryl-alkyl group in which the aryl and alkyl group are previously defined. Exemplary aralkyl groups include benzyl and phenethyl.

Alkenyl as used herein means a branched or straight chain having from 2 to 12 carbon atoms and more preferably from 2 to 6 carbon atoms, the chain containing at least one carbon-carbon double bond. Alkenyl, may be used synonymously with the term olefin and includes alkylidenes. Exemplary alkenyl groups include ethylene, propylene and isobutylene.

Alkanoyl as used herein refers to —C(O)alkyl where alkyl is as previously defined.

Alkenoyl as used herein refers to —C(O)alkenyl where alkenyl as previously defined.

Alkoxy as used herein means an —O-alkyl group in which the alkyl group is as previously described. Exemplary alkoxy groups include methoxy, ethoxy, n-propoxy, i-propoxy, n-butoxy, and t-butoxy.

Arylalkanoyl as used herein refers to a carbonyl group or radical directly bonded to an alkyl group of 1 to 10 carbon atoms which is terminally substituted by an aryl group as previously defined, for example phenylacetic acid. The aryl group may optionally be substituted with one to three substituents each independently selected from the group halogen, cyano, alkyl of 1 to 10 carbon atoms, alkoxy of 1 to 10 carbon atoms, $CF_3$, and phenyl and substituted phenyl where the substituents are selected from halogen, cyano, alkyl of 1 to 10 carbon atoms, alkoxy of 1 to 10 carbon atoms and —$CF_3$.

Arylalkenoyl as used herein refers to a carbonyl group or radical directly bonded to an alkenyl group of 2 to 12 carbon atoms which is terminally substituted by an aryl group as previously defined. The aryl group may optionally be substituted with one to three substituents each independently selected from the group halogen, cyano, alkyl of 1 to 10 carbon atoms, alkoxy of 1 to 10 carbon atoms, —$CF_3$, and phenyl and substituted phenyl where the substituents are selected from halogen, cyano, alkyl of 1 to 10 carbon atoms, alkoxy of 1 to 10 carbon atoms and —$CF_3$.

Alkylsulfonyl as used herein refers to the radical —$SO_2$alkyl where alkyl is as previously defined.

Arylsulfonyl as used herein refers to the radical —$SO_2$aryl where aryl is as previously defined.

Arylalkylsulfonyl as used herein refers to the radical arylalkyl$O_2$S- where arylalkyl is as previously defined.

Phenyl as used herein refers to a 6-membered aromatic ring.

Where terms are used in combination, the definition for each individual part of the combination applies unless defined otherwise. For instance, aralkyl refers to an aryl group, and alkyl refers to the alkyl group as defined above.

The range of carbon atoms defines the number of carbons in the carbon backbone and does not include carbon atoms occurring in substituent groups.

The present invention also provides a process for the preparation of compounds of Formulae (I) and (II). Compounds of Formulae (I) and (II) wherein X is —O— and Y is —$NR_4$, where $R_4$ is as defined above, may be prepared as shown in Scheme 1. Treatment of an appropriately substituted benzofuranone 1 where $R_1$, $R_2$ and $R_3$ are hereinbefore defined with 2-hydrazinobenzoic acid 2 in aqueous media affords the corresponding phenyl hydrazone 3. This intermediate is either isolated and purified and then converted, or subjected crude to a microwave-facilitated Fischer-indole cyclization in an acidic media such as, but not limited to, formic acid to yield the substituted benzo[4,5]furo[3,2-b]indole 4. Standard procedures may then be utilized to introduce $R_4$ when $R_4$ is not a hydrogen atom to prepare carboxylic acid 5.

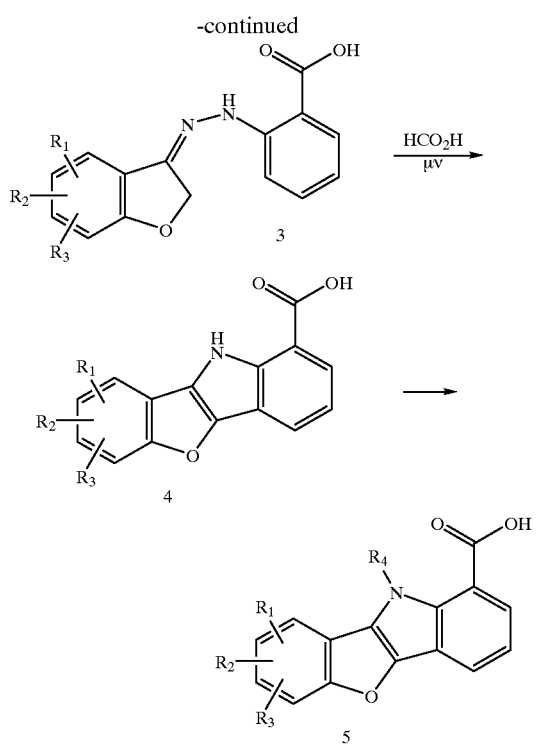

Alternatively, for examples represented by Formulae (I) and (II) wherein X is —$NR_4$, and Y is —$CR_5R_6$, where $R_4$, $R_5$ and $R_6$ are as defined above, may be prepared as shown in Scheme II. An appropriately substituted phenylhydrazine (6) where $R_1$, $R_2$ and $R_3$ are hereinbefore defined may be treated with an indanone-1-carboxylic acid (7) where $R_5$ and $R_6$ are hereinbefore defined to afford phenyl hydrazone (8) which is further reacted in the presence of an acid, such as, but not limited to, formic acid in a microwave-facilitated Fischer-indole cyclization to yield indeno[1,2-b]indole 9.

Scheme II

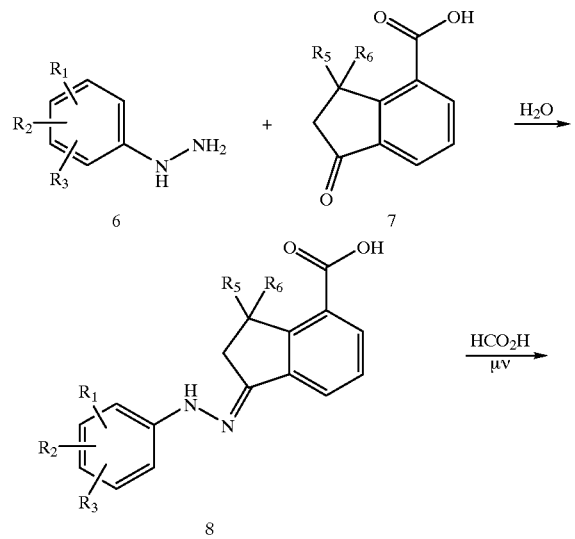

Scheme 1

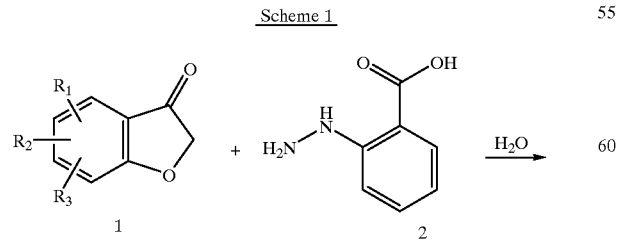

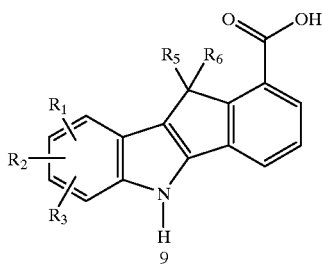

9

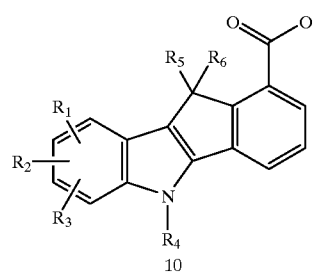

10

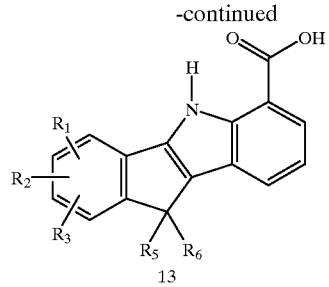

13

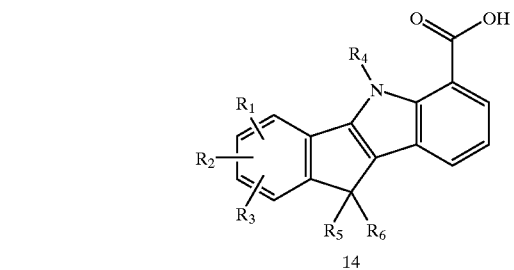

14

Standard procedures may then be utilized to introduce $R_4$ when $R_4$ is not a hydrogen atom to give carboxylic acid 10.

Compounds of Formulae (I) and (II) wherein X is —$CR_5R_6$, and Y is —$NR_4$, where $R_4$, $R_5$ and $R_6$ are as defined above, may be prepared as shown in Scheme III. An appropriately substituted indanone (11) where $R_1$, $R_2$, $R_3$, $R_5$ and $R_6$ are hereinbefore defined may be treated with 2-hydrazinobenzoic acid (2) in aqueous media to afford intermediate phenylhydrazone (12). Intermediate phenylhydrazone can be subjected to microwave radiation to facilitate a Fischer-indole cyclization in an acidic media such as, but not limited to, formic acid to yield the substituted indeno [1,2-b] indole (13). Standard procedures may then be utilized to introduce $R_4$ when $R_4$ is not a hydrogen atom to give carboxylic acid 14.

Scheme III

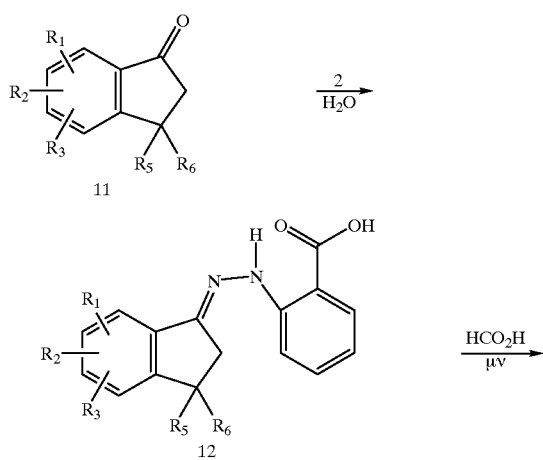

The carboxylic acid moiety of substituted benzo [4,5]furo [3,2-b]indole 4, carboxylic acid 5, indeno[1,2-b]indole 9, carboxylic acid 10, substituted indeno[1,2-b]indole 13 and carboxylic acid 14 may be elaborated into other groups represented by Z in Formulae (I) and (II). For example, treatment with an alkaline base or alkaline earth base will result in formation of the corresponding carboxylate salts. Treatment with an alcohol ($R_7OH$, where $R_7$ is as described above) in the presence of acid will result in formation of an ester. Esters may also be formed by other methods known to those versed in the art.

Reduction of the ester with an appropriate reducing agent such as diisobutylaluminum hydride, sodium borohydride, lithium aluminum hydride will afford the corresponding alcohol or aldehyde. If only the alcohol is formed, it may be oxidized to the aldehyde with an appropriate mild oxidant such as pyridinium chlorochromate or 1,1,1-triacetoxy-1,1-dihydro-1,2-benziodoxol-3(1H)-one, or tetrapropoylammonium perruthenate in acetonitrile in the presence of 4 Å sieves.

The carboxylic acid moiety may also be converted to the corresponding amide by treatment with an amine-($NHR_8R_9$, where $R_8$ and $R_9$ are as described above) in the presence of an activating agent such as 2-dimethylaminoisopropyl chloride hydrochloride/4-dimethylaminopyridine, or diethyl azodicarboxylate/triphenyl phosphine. Alternatively, the carboxylic acid may be converted to the corresponding acid chloride derivative using an approprate agent such as thionyl chloride or oxalyl chloride. Treatment with the appropriate amine-($NHR_8R_9$, where $R_8$ and $R_9$ are as described above) in the presence of an external base would then afford the desired amide.

In a similar manner, the corresponding hydroxamic acid may be prepared by treatment of the acid chloride derivative with an appropriately substituted hydroxylamine ($NHR_8OH$, where $R_8$ is as described above). Treatment of the carboxylic acid with urea in the presence of strong acid will provide the corresponding nitrile (Z is CN). The nitrile may be converted to a tetrazole via a cyclization reaction with sodium azide.

Alkylation of the carboxylic acid with $Cl(R_{10})COC(O)$ $R_{11}$ using the conditions as described by Kim, K. S. et al. *J. Med. Chem.* 1993, 36, 2335 in the presence of an appropriate base or $Ag_2O$ in a solvent such as tetrahydrofuran or dichloromethane; or with $ClCH_2C(O)N(R_{12}R_{13})$ using the conditions as reported by Bundgaard, H. *Int. J. Pharm.* 1989, 55, 91 in the presence of sodium iodide/N,N-dimethylformamide and an appropriate base, will afford the bioequivalent prodrug analogs.

The compounds of Formulae (I) and (III) and their pharmaceutically acceptable salts relax smooth muscle. They are therefore useful in the treatment of disorders associated with smooth muscle contraction, disorders involving excessive smooth muscle contraction of the urinary tract (such as incontinence), or of the gastro-intestinal tract (such as irritable bowel syndrome), asthma, and hair loss. Furthermore, the compounds of Formulae (I) and (II) are active as potassium channel activators which render them useful for treatment of peripheral vascular disease, congestive heart failure, stroke, anxiety, cerebral anoxia and other neurodegenerative disorders.

Compounds of the present invention potently relax smooth muscle in standard pharmacological tests. The compounds of this invention exert their smooth muscle relaxatory activity via activation of potassium channels. In addition, the compounds of the present invention are unique in that they possess intrinsic selectivity for bladder tissue over vascular tissue as demonstrated by bladder/aorta $IC_{50}$ ratios (Table 1).

The present invention also provides a pharmaceutical composition which comprises a compound of this invention in combination or association with a pharmaceutically acceptable carrier. In particular, the present invention provides a pharmaceutical composition which comprises an effective amount of a compound of this invention and a pharmaceutically acceptable carrier.

The compositions are preferably adapted for oral administration. However, they may also be adapted for other modes of administration, for example, parenteral administration for patients suffering from heart failure.

In order to obtain consistency of administration, it is preferred that a composition of the invention is in the form of a unit dose. Suitable unit dose forms include tablets, capsules and powders in sachets or vials. Such unit dose forms may contain from 0.1 to 100 mg of a compound of the invention and preferably from 2 to 50 mg. Still further preferred unit dosage forms contain 5 to 25 mg of a compound of the present invention. The compounds of the present invention can be administered orally at a dose range of about 0.01 to 100 mg/kg or preferably at a dose range of 0.1 to 10 mg/kg. Such compositions may be administered from 1 to 6 times a day, more usually from 1 to 4 times a day.

The compositions of the invention may be formulated with conventional excipients, such as a filler, a disintegrating agent, a binder, a lubricant, a flavoring agent and the like. They are formulated in conventional manner, for example, in a manner similar to that used for known antihypertensive agents, diuretics and β-blocking agents.

The present invention further provides a compound of the invention for use as an active therapeutic substance. Compounds of Formula (I) and (II) are of particular use in the induction of smooth muscle relaxation.

The present invention further provides a method of treating smooth muscle disorders in mammals including man, which comprises administering to the afflicted mammal an effective amount of a compound or a pharmaceutical composition of the invention.

The following examples are presented to illustrate rather than limit the methods for production of representative compounds of the invention.

EXAMPLE 1

8-Bromo-10H-benzo[4,5]furo[3,2-b]indole-1-carboxylic acid

Step 1) Preparation of o-[(2,3-dihydro-5-bromobenzofuran-3-ylidene)hydrazino]-benzoic acid To a solution of 5-bromo-3(2H)-benzofuranone (3.10 g, 14.6 mmol) [Ellingboe, J. et al., *J. Med. Chem.* 1992,35 (7), 1176–1183] in ethanol (100 mL) was added a solution of 2-hydrazinobenzoic acid hydrochloride (5.49 g, 29.1 mmol) in deionized water (200 mL). The mixture was stirred for one hour at room temperature and then allowed to sit while cooled (0° C.). Vacuum filtration and drying in vacuo afforded 3.65 g (72%) of the title compound as a brown solid: mp 195° C.(dec) which was used without further purification.

Step 2) Preparation of 8-Bromo-10H-benzo[4,5]furo[3,2-b]indole-1-carboxylic acid The hydrazone (from Step 1, Example 1 above) (0.500 g, 1.51 mmol) in formic acid (2 mL, 96%) was irradiated for two minutes in a closed cap Teflon vessel in a microwave oven (700 W). The mixture was vacuum filtered hot and the solid was dried in vacuo to yield 0.271 g (57%) of the title compound as a yellow solid: mp 312–313° C.; 1H NMR (DMSO-d6): δ 13.36 (s, 1H), 11.64 (s, 1H), 8.27 (s, 1H), 8.07 (d, 1H), 7.92 (d, 1H), 7.70 (d, 1H), 7.50 (d, 1H), 7.27 (t, 1H); IR (KBr): 3420, 1685 $cm^{-1}$; MS (m/z) 329 (M+).

Elemental analysis for $C_{15}H_8BrNO_3$

Calc'd: C, 54.57; H, 2.44; N, 4.24.

Found: C, 54.22; H, 2.32; N, 4.30.

EXAMPLE 2

8-Iodo-10H-benzo[4,5]furo[3,2-b]indole-1-carboxylic acid

Step 1) Preparation of o-[(2,3-dihydro-5-iodobenzofuran-3-ylidene)hydrazino]-benzoic acid To a solution of 5-iodo-3(2H)-benzofuranone (0.551 g, 2.12 mmol) [Cagniant, P. et al. *Hebd. Seances Acad. Sci., Ser. C,* 1976, 282 (21), 993–6] in ethanol (100 mL) was added a solution of 2-hydrazinobenzoic acid hydrochloride (0.800 g, 4.24 mmol) in deionized water (50 mL). The mixture was stirred for one hour at room temperature and then allowed to sit while cooled (0° C.). Vacuum filtration and drying in vacuo afforded 0.480 g (58%) of the title compound as a tan solid: mp 169° C.(dec) which was used without further purification.

Step 2)Preparation of 8-iodo-10H-benzo[4,5]furo[3,2-b]indole-1-carboxylic acid

The hydrazone (from Step 1, Example 2 above) (0.480 g, 1.22 mmol) in formic acid (2 mL, 96%) was irradiated for two minutes in a closed cap Teflon vessel of a microwave oven (700 W). The mixture was vacuum filtered hot and the solid was dried in vacuo to yield 0.240 g (52%) of the title compound as a yellow solid: mp 297° C.(dec); $^1$H NMR (DMSO-d6): δ 13.33 (s, 1H), 11.63 (s, 1H), 8.47 (s, 1H), 8.07 (d, 1H), 7.91 (d, 1H), 7.65 (d, 1H), 7.57 (d, 1H), 7.28 (t, 1H); IR (KBr): 3420, 1670 $cm^{-1}$; MS (m/z) 377 (M+).

Elemental analysis for $C_{15}H_8INO_3$

Calc'd: C, 47.77; H, 2.14; N, 3.71.

Found: C, 47.61; H, 1.92; N, 3.68.

EXAMPLE 3

8-Chloro-10H-benzo4,5]furo[3,2-b]indole-1-carboxylic acid

Step 1) Preparation of o-[(2,3-dihydro-5-chlorobenzofuran-3-ylidene)hydrazino]-benzoic acid To a solution of 5-chloro-3(2H)-benzofuranone (0.357 g, 2.12 mmol) [Ellingboe, J. et al. *J. Med. Chem.* 1992, 35 (7), 1176–1183] in ethanol (100 mL) was added a solution of 2-hydrazinobenzoic acid hydrochloride (0.800 g, 4.24 mmol) in deionized water (50 mL). The mixture was stirred for one hour at room temperature and then allowed to sit while cooled (0° C.). Vacuum filtration and drying in vacuo afforded 0.400 g (62%) of the title compound as a pale yellow solid: mp 190° C.(dec) which was used without further purification.

Step 2) Preparation of 8-chloro-10H-benzo[4,5]furo[3,2-b]indole-1-carboxylic acid The hydrazone (from Step 1, Example 3 above) (0.400 g, 1.32 mmol) in formic acid (2 mL, 96%) was irradiated for two minutes in a closed cap Teflon vessel of a microwave oven (700 W). The mixture was vacuum filtered hot and the solid was dried in vacuo to yield 0.220 g (58%) of the title compound as a yellow solid: mp 303° C.(dec); $^1$H NMR (DMSO-d6): δ 13.24 (s, 1H), 11.64 (s, 1H), 8.12 (s, 1H), 8.07 (d, 1H), 7.92 (d, 1H), 7.75 (d, 1H), 7.39 (d, 1H), 7.28 (t, 1H); IR (KBr): 3430, 1685 cm$^{-1}$; MS (m/z) 285 (M$^+$).

Elemental analysis for $C_{15}H_8ClNO_3$

Calc'd: C, 63.06; H, 2.82; N, 4.90.

Found: C, 63.00; H, 2.57; N, 4.98.

EXAMPLE 4

8-Nitro-10H-benzo[4,5]furo[3,2-b]indole-1-carboxylic acid dihydrate

Step 1) Preparation of o-[(2,3-dihydro-5-nitrobenzofuran-3-ylidene)hydrazino]-benzoic acid 5-Nitro-3(2H)-benzofuranone (0.500 g, 2.79 mmol) [Tobias, P. et al. *J. Amer. Chem. Soc.,* 1969, 91 (18), 5171–5173] and 2-hydrazinobenzoic acid hydrochloride (0.526 g, 2.79 mmol) were combined in pyridine (10 mL) and stirred overnight at ambient temperature. The mixture was vacuum filtered and dried in vacuo to afford 0.800 g (86%) of title compound as a yellow solid: mp 210° C.(dec) which was used without purification.

Step 2) Preparation of 8-Nitro-10H-benzo[4,5]furo[3,2-b]indole-1-carboxylic acid dihydrate The hydrazone (from Step 1, Example 4 above) (0.500 g, 1.51 mmol) in formic acid (2 mL, 96%) was irradiated for two minutes in a closed cap Teflon vessel of a microwave oven (700 W). The mixture was vacuum filtered and the solid was dissolved in dimethylsulfoxide and re-precipitated with water to yield 0.296 g (66%) of the title compound as a yellow solid: mp 325° C.(dec); $^1$H NMR (DMSO-d6): δ 13.42 (s, 1H), 11.82 (s, 1H), 9.07 (d, 1H), 8.26 (d, 1H), 8.13 (d, 1H), 7.97 (d, 1H), 7.95 (s, 1H), 7.32 (t, 1H); IR (KBr): 3380, 1675 cm$^{-1}$; MS (m/z) 296 (M$^+$).

Elemental analysis for $C_{15}H_8N_2O_5 \cdot 2 H_2O$

Calc'd: C, 54.22; H, 3.64; N, 8.43.

Found: C, 54.25; H, 3.48; N, 7.68.

EXAMPLE 5

8-Bromo-10H-benzo[4,5]furo[3,2-b]indole-1-carboxylic acid amide

The product of Example 1, Step 2 (0.100 g, 0.303 mmol) was dissolved in diethyl ether (20 mL). To this solution under argon was added phosphorus pentachloride (72.0 mg, 0.345 mmol). After stirring at room temperature for 30 minutes a yellow precipitate formed. Diethyl ether saturated with ammonia (75 mL) was added and reaction was allowed to stir overnight. The mixture was concentrated and chromatographed (hexane/ethyl acetate, 1:1) collecting the higher eluting amide (60 mg). The isolated product was triturated with diethyl ether to yield 0.024 g (24%) of the title compound as a pale yellow solid: mp 300–301° C.; $^1$H NMR (DMSO-d6): δ 11.72 (s, 1H), 8.31 (s, 1H), 8.24 (br s, 1H), 7.97 (d, 1H), 7.82 (d, 1H), 7.68 (d, 1H), 7.58 (br s, 1H), 7.47 (d, 1H), 7.22 (t, 1H); IR (KBr): 1650 cm$^{-1}$; MS (m/z) 328 (M+)

Elemental analysis for $C_{15}H_9BrN_2O_2$

Calc'd: C, 54.74; H, 2.75; N, 8.51.

Found: C, 54.53; H, 2.72; N, 8.34.

EXAMPLE 6

8-Bromo-10H-benzo[4,5]furo[3,2-b]indole-1-carboxylic acid methyl ester

The product of Example 1, Step 2 (5.75 g, 17.4 mmol) was combined with concentrated sulfuric acid (3 mL) and methanol (500 mL) and heated in an oil bath (100° C.) for three days. The mixture was cooled and concentrated to a residue. The residue was triturated with diethyl ether to yield 2.40 g (40%) of title compound as a tan solid: mp 204–205° C.; $^1$H NMR (DMSO-d6): δ 11.66 (s, 1H), 8.23 (s, 1H), 8.10 (d, 1H), 7.93 (d, 1H), 7.71 (d, 1H), 7.52 (d, 1H), 7.30 (t, 1H), 4.01 (s, 3H); IR (KBr): 3420, 1710 cm$^{-1}$; MS (m/z) 343 (M$^+$).

Elemental analysis for $C_{16}H_{10}BrNO_3$

Calc'd: C, 55.84; H, 2.93; N, 4.07.

Found: C, 55.49; H, 2.82; N, 4.01.

EXAMPLE 7

(8-Bromo-10H-benzo[4,5]furo[3,2-b]indol-1-yl)-methanol

To a solution of the product of Example 6 (0.196 g, 0.570 mmol) in tetrahydrofuran (5 mL) was added lithium aluminum hydride powder (0.025 g, 0.659 mmol). After stirring at ambient temperature for 18 h, deionized water (0.20 mL) was carefully added, followed by 2.5 N sodium hydroxide (0.20 mL), and then water (2 mL). The mixture was filtered through a pad of diatomaceous earth and the filtrate was dried with magnesium sulfate. The crude product was subjected to chromatography (hexane/ethyl acetate, 3:1) to yield 0.060 g (33%) of the title compound as a white solid: mp 218–219° C.; $^1$H NMR (DMSO-d6): δ 11.25 (s, 1H), 8.01 (s, 1H), 7.68 (d, 2H), 7.49 (d, 1H), 7.25 (d, 1H), 7.14 (t, 1H), 5.38–5.41 (br s, 1H), 4.88 (s, 2H); IR (KBr): 3600–3100 (broad) cm$^{-1}$; MS (m/z) 315 (M$^+$).

Elemental analysis for $C_{15}H_{10}BrNO_2$

Calc'd: C, 56.99; H, 3.19; N, 4.43.

Found: C, 57.23; H, 2.45; N, 4.45.

EXAMPLE 8

8-Bromo-10H-benzo[4,5]furo[3,2-b]indole-1-carboxylic acid hydroxy-methyl amide

To a solution of the product of Example 1, Step 2 (1.00 g, 3.03 mmol) in diethyl ether (100 mL) and N,N-dimethylformamide (0.40 mL) was added oxalyl chloride (1.00 mL, 11.5 mmol). After one hour the yellow mixture was concentrated in vacuo. The residue was dissolved in dichloromethane (80 mL) and added to a stirring mixture of N-methyl hydroxylamine hydrochloride (1.26 g, 15.1 mmol) in tetrahydrofuran/water (16 mL, 15:1) and triethylamine (4.20 mL, 30.3 mmol). After stirring overnight the mixture was partitioned between ethyl acetate and water. The organic phase was dried with magnesium sulfate. The crude product was subjected to chromatography (hexane/ethyl acetate, 1:1) to yield 0.100 g (9%) of the title compound as a white solid: mp 174–175° C.; $^1$H NMR (DMSO-d6): δ 10.22–11.18 (br s, 2H), 8.12 (s, 1H), 7.88 (d, 1H), 7.69 (d, 1H), 7.65 (d, 1H), 7.50 (d, 1H), 7.20 (t, 1H), 3.38 (s, 3H); IR (KBr): 1640 cm$^{-1}$; MS (m/z) 358 (M$^+$).

Elemental analysis for $C_{16}H_{11}BrN_2O_3$
  Calc'd: C, 53.50; H, 3.09; N, 7.80.
  Found: C, 53.33; H, 2.98; N, 7.71.

EXAMPLE 9

8-Bromo-10H-benzo[4,5]furo[3,2-b]indole-1-carbaldehyde

To a solution of the product of Example 7 (0.390 g, 1.23 mmol) in acetonitrile (50 mL) was added a solution of 1,1,1-triacetoxy-1,1-dihydro-1,2-benziodoxol-3(1H)-one (0.522 g, 1.23 mmol) in acetonitrile (20 mL). Reaction was monitored by TLC (hexane/ethyl acetate, 1:1). The yellow mixture was poured into a saturated solution of sodium bicarbonate containing sodium thiosulfate (0.187 g, 1.18 mmol). The mixture was partitioned and the organic phase was washed with aqueous sodium bicarbonate and brine, dried (MgSO$_4$), then concentrated to a residue. Trituration afforded a solid which was dried in vacuo to yield 0.117 g (30%) of the title compound as a yellow solid: mp 280–281° C.; $^1$H NMR (DMSO-d6): δ 12.10 (s, 1H), 10.23 (s, 1H), 8.24 (s, 1H), 8.20 (d, 1H), 7.96 (d, 1H), 7.73 (d, 1H), 7.54 (d, 1H),7.43 (t, 1H); IR (KBr): 1660 cm$^{-1}$; MS (m/z) 313 (M$^+$).

Elemental analysis for $C_{15}H_8BrNO_2$
  Calc'd: C, 57.35; H, 2.57; N, 4.46.
  Found: C, 57.05; H, 2.37; N, 4.86.

EXAMPLE 10

8-Bromo-10H-benzo[4,5]furo[3,2-b]indole-1-carbonitrile hydrate

The product of Example 1, Step 2 (0.500 g, 1.51 mmol) was thoroughly mixed with ground urea powder (8.67 g, 144 mmol). Phosphoric acid (2.5 g, 21.7 mmol) was added, followed by N,N-dimethylformamide (DMF) (7 mL). The reaction mixture was irradiated in a microwave oven for a total of 35 minutes (15–30% power, 700 W), then cooled. Crude product was ground and partitioned between water and diethyl ether. The organic phase was concentrated in vacuo and the residue was dissolved in acetone/diethyl ether (1:1) and filtered through a plug of silica gel and eluted with diethyl ether and hexane (1:1) to afford 0.088 g (19%) of the title compound as a pale yellow solid: mp 277–280° C.(dec); $^1$H NMR (DMSO-d6): δ 11..44 (s, 1H), 8.18 (d, 1H), 7.97 (s, 1H), 7.79 (d, 1H), 7.76 (d, 1H), 7.58 (d, 1H), 7.34 (t, 1H); IR (KBr): 2230 cm $^{-1}$.

Elemental analysis for $C_{15}H_7BrN_2O \cdot H_2O$
  Calc'd: C, 54.74; H, 2.76; N, 8.51.
  Found: C, 55.29; H, 2.36; N, 8.22.

EXAMPLE 11

8-Bromo-1-(1H-tetrazol-5-yl)-10H-benzo[4,5]furo[3,2-b]indole

The product of Example 10 (0.350 g, 1.13 mmol), NaN$_3$ (0.102 g, 1.58 mmol), and n-Bu$_3$SnCl (0.43 mL, 1.58 mmol) were stirred together in xylenes (5 mL) at 120° C. for 18 h. The reaction was monitored by TLC and DMF (2 mL) was added. The reaction was stirred an additional 18 h at 130° C. The reaction mixture was cooled and diluted with 6N HCl (10 mL) and stirred for 1 h while purging with N$_2$ gas. A solid formed and was vacuum filtered and washed with H$_2$O. The solid was recrystallized from hot methanol and then was triturated with hot ethyl acetate. The title compound (0.15 g, 38%) was collected by filtration as an off-white solid: mp 275–277° C. (dec); $^1$H NMR (DMSO-d6): δ 11.87 (s, 1 H), 8.41 (d, 1 H), 8.05 (d, 1 H), 7.97 (d, 1 H), 7.71 (d, 1 H), 7.54 (d, 1 H), 7.41 (dd, 1 H); IR (KBr): 3360, 1440 cm$^{-1}$; MS (m/z) 353 (M$^+$).

Elemental analysis for $C_{15}H_8BrN_5O$
  Calc'd: C, 50.87; H, 2.27; N, 19.77.
  Found: C, 50.93; H, 2.52; N, 18.06.

EXAMPLE 12

8-Bromo-10H-benzo[4,5]furo[3,2-b]indole-1-carboxylic acid (1,2,2-trimethyl-propyl)-amide To the product of Example 1, Step 2 (0.15 g, 0.455 mmol) in dichloromethane (4 mL) was added 5 drops of DMF followed by oxalyl chloride (0.12 mL, 1.53 mmol). The mixture was stirred for 1 h at room temperature and concentrated in vacuo. The residue was re-dissolved in dichloromethane (5 mL) and to the solution was added 3,3-dimethyl-2-aminobutane (0.134 mL, 1.00 mmol). The reaction mixture was stirred for 4 h and was concentrated in vacuo to a residue. The residue was partitioned between aqueous Na$_2$CO$_3$ and ethyl acetate. The organic phase was dried and decolorized. Concentration afforded a residue which was triturated with hexanes to give 0.07 g (37%) of title amide as an off-white solid: mp 173–175° C.; $^1$H NMR (DMSO-d6): δ 11.69 (s, 1 H), 8.26 (s, 1 H), 8.19 (d, 1 H), 7.97 (d, 1 H), 7.87 (d, 1 H), 7.67 (d, 1 H), 7.50 (d, 1 H), 7.24 (m, 1 H), 4.14 (m, 1 H), 1.17 (d, 3 H), 0.96 (s, 9 H); IR (KBr): 3390, 3300, 2960, 1640 cm$^{-1}$; MS (m/z) 412 (M$^+$).

Elemental analysis for $C_{21}H_{21}BrN_2O_2$
  Calc'd: C, 61.03; H, 5.12; N, 6.78.
  Found: C, 59.97; H, 5.32; N, 7.10.

EXAMPLE 13

8-Bromo-10H-benzo[4,5]furo[3,2-b]indole-1-carboxylic acid (1,1-dimethyl-propyl)-amide To a heterogeneous mixture of the product of Example 1, step 2 (300 mg, 909 mmol) in anhydrous N,N-dimethylformamide (281 µL) and CH$_2$Cl$_2$ (9.0 mL) at 0° C. was added oxalyl chloride (317 µL, 3.63 mmol). Upon cessation of gas evolution, the mixture was warmed to room temperature and stirred for 1 h, then cooled to 0° C. whereupon tert-amyl amine (425 µL, 3.63 mmol) was added. The reaction mixture was stirred for 12 h, whereupon all volatiles were removed by rotary evaporation. The solid residue was dissolved in hot acetone-ethanol (8:1, 50 mL), filtered to give a clear solution to which was added water (50 mL) to induce precipitation. Filtration followed by drying under high vacuum at 50° C. afforded 111 mg (30%) of the title compound as an off-white solid: mp 242–244 ° C. (dec ); $^1$H NMR (DMSO-d6) δ 11.66 (s, 1H), 8.28 (d, 1H), 7.94 (d, 1H), 7.83 (d, 1H), 7.77 (s, 1H), 7.68 (d, 1 H), 7.48 (dd, 1H), 7.21 (dd, 1H), 1.90 (q, 2H), 1.42 (s, 6H), 0.87 (t, 3H); IR (KBr) 3420, 3340, 2990, 1650, 1590, 1520, 1430, 1380, 1280, 1190, 1160, 980, 800, 750 cm$^{-1}$; MS (m/z) 398/400 (M$^+$).

Elemental analysis for $C_{20}H_{19}BrN_2O_2$
  Calc'd: C, 60.16; H, 4.79; N, 7.02.
  Found: C, 59.53; H, 4.35; N, 6.88.

EXAMPLE 14

8-Bromo-10H-benzo[4,5]furo[3,2-b]indole-1-carboxylic acid methylamide

To a heterogeneous mixture of the product of Example 1, step 2 (300 mg, 909 mmol) in anhydrous N,N- dimethylformamide (281 μL) and CH$_2$Cl$_2$ (9.0 mL) at 0° C. was added oxalyl chloride (317 μL, 3.63 mmol). Upon cessation of gas evolution, the mixture was warmed to room temperature and stirred for 1 h, then cooled to 0° C. whereupon methylamine (approx. 4–5 mL) was added. The reaction mixture was stirred for 12 h, at which point all volatiles were removed via rotary evaporation. The solid residue was submitted to ultrasonication in acetonitrile (10 mL), filtered, then washed sparingly with acetonitrile. The solid was then dissolved in hot acetone-ethanol (8:1, 50 mL), filtered, and precipitation was induced by addition of water (50 mL) while sonicating. Filtration followed by drying under high vacuum at 50° C. afforded 55 mg (18%) of the title compound as a white solid: mp 264–265° C. (dec ); $^1$H NMR (DMSO-d6) δ 11.74 (s, 1H), 8.66 (q, 1H), 8.27 (d, 1H), 7.95 (d, 1H), 7.76 (d, 1H), 7.68 (d, 1H), 7.49 (dd, 1H), 7.23 (dd, 1H), 2.90 (d, 3H); IR (KBr) 3460, 3310, 3060, 1680, 1630, 1590, 1560, 1450, 1440, 1410, 1380, 1330, 1290, 1200, 1160, 1150, 1050, 860, 810, 750 cm$^{-1}$; MS (m/z) 344/342 (M+).

Elemental analysis for $C_{16}H_{11}BrN_2O_2$

Calc'd: C, 56.00; H, 3.23; N, 8.16.

Found: C, 55.73; H, 3.08; N, 7.99.

EXAMPLE 15

8-Bromo-10-methyl-10H-benzo[4,5]furo[3,2-b]indole-1-carboxylic acid methyl ester To a homogeneous solution of the product from Example 1, step 2 (1.78 g, 5.40 mmol) in N,N-dimethylformamide (20 mL) at −5° C. was added portionwise 80% sodium hydride (324 mg, 10.8 mmol). The resultant red mixture was stirred for 1 h while slowly warming to room temperature, whereupon it was treated with methyl trifluoromethanesulfonate (1.83 mL, 16.2 mmol), producing a copious precipitate. Additional N,N-dimethylformamide (5 mL) was added to facilitate stirring. The reaction mixture was stirred an additional 1 h, then diluted with water, filtered, and washed consecutively with water and methanol. The solid material was recrystalized from acetone-water, filtered, then dried under high vacuum at 50° C. affording 357 mg (19%) of a white solid: mp 195–196° C.; $^1$H NMR (DMSO-d6) δ 8.31 (d, 1H), 8.04 (dd, 1H), 7.74 (d, 1H), 7.68 (dd, 1H), 7.56 (dd, 1H), 7.29 (dd, 1H), 4.04 (s, 3H), 3.97 (s, 3H); IR (KBr) 3430, 2980, 1720, 1465, 1435, 1270, 1165, 1105, 1080, 940, 790, 755, 730 cm$^{-1}$; MS (m/z) 357/359 (M+).

Elemental analysis for $C_{17}H_{12}BrNO_3$

Calc'd: C, 57.00; H, 3.38; N, 3.91.

Found: C, 56.83; H, 3.17; N, 3.83.

EXAMPLE 16

10H-Benzo[4,5]furo[3,2-b]indole-1-carboxylic acid

To a homogeneous solution of 3-coumaranone (2.63 g, 20 mmol) in ethanol (50 mL) was added dropwise a solution of phenyl hydrazine-2-carboxylic acid hydrochloride (6.79 g, 36 mmol)in water (75 mL). The resultant mixture was stirred for 12 h at room temperature, filtered, then dried in vacuo, affording 2.17 g (40%) of the corresponding hydrazone as a white solid.

A suspension of the above phenylhydrazone (268 mg, 1.0 mmol) in formic acid (5.0 mL) was heated to 110° C. at which point the mixture became homogeneous, followed by the formation of a copious precipitate. Heating of the reaction mixture was continued for an additional 5 min, cooled in an ice bath and the solid collected. The solid was washed with water, recrystallized from acetone-water, and then dried in vacuo affording 156 mg (62%) of a yellow solid: mp 279–280° C. (dec); 1H NMR (DMSO-d6) δ 13.28 (m, 1H), 11.65 (s, 1H), 8.09 (ddd, 2H), 7.89 (dd, 1H), 7.71 (m, 1H), 7.36 (m, 2H), 7.26 (d, 1H); IR (KBr) 3420, 3000 (br), 1670, 1600, 1435, 1290, 750, 720 cm$^{-1}$; MS (m/z) 251 (M+).

Elemental analysis for $C_{15}H_9NO_3$

Calc'd: C, 71.71; H, 3.61; N, 5.57.

Found: C, 71.83; H, 3.39; N, 5.47.

EXAMPLE 17

8-Iodo-5,10-dihydro-indeno[1,2-b]indole-1-carboxylic acid 0.6 hydrate

1-Oxo-indan4-carboxylic acid (0.528 g, 2.99 mmol) and 4-iodophenylhydrazine hydrochloride (0.698 g, 2.58 mmol) were mixed together in a Teflon PFA vessel to form a paste in formic acid (2 mL, 96%) containing 3 drops of concentrated HCl. The vessel was irradiated at full power (760 W) in a CEM Microwave (MDS2000) for one minute (T=140 C, P<50 PSI), allowed to cool for 2 min, then irradiated again for one min (T=140 C, P<50 PSI). The mixture was vacuum filtered hot. The solid was washed with formic acid, and dried on the frit. Chromatography (acetone/hexane) and trituration with diethyl ether gave the title compound (0.059 g, 5%) as an tan solid: mp 251° C.; $^1$H NMR (DMSO-d6): δ 3.98 (s, 2H), 7.30–7.37 (m, 2H), 7.49 (t, 1H), 7.77–7.80 (m, 2H), 7.98 (d, 1H), 11.82 (s, 1H), 13.53 (s, 1H); MS [EI, m/z]: 375 [M]+.

Elemental analysis for $C_{16}H_{10}INO_2 \cdot 0.6(H_2O)$

Calc'd: C, 49.87; H, 2.72; N, 3.63

Found: C, 49.59; H, 2.81; N, 3.66

EXAMPLE 18

8-Sulfamoyl-5,10-dihydro-indeno[1,2-b]indole-1-carboxylic acid hemi-hydrate

In a manner similar to Example 17, 1-oxo-indan-4-carboxylic acid (0.528 g, 2.99 mmol) and 4-sulfamoylphenylhydrazine hydrochloride (0.671 g, 3.0 mmol) were converted to the title compound (0.240 g, 5%) as a tan solid: mp 270–272° C. (dec); $^1$H NMR (DMSO-d6): δ 4.07 (s, 2H), 7.15 (br s, 2H), 7.52 (t, 1H), 7.59–7.63 (m, 2H), 7.80–7.85 (m, 2H), 8.11 (d, 1H), 12.10 (s, 1H), 13.13 (s, 1H); MS [EI, m/z]: 328 [M]+.

Elemental analysis for $C_{16}H_{12}N_2O_4S \cdot 0.5(H_2O)$

Calc'd: C, 56.97; H, 3.88; N, 8.30

Found: C, 56.71; H, 3.49; N, 8.19

EXAMPLE 19

8-Fluoro-5,10-dihydro-indeno[1,2-b]indole-1-carboxylic acid

In a manner similar to Example 17, 1-oxo-indan-4-carboxylic acid (1.00 g, 5.68 mmol) and 4-fluorophenylhydrazine hydrochloride (0.923 g, 5.68 mmol) were converted to the title compound (0.140 g, 10%) as an off-white solid: mp>300° C.; $^1$H NMR (DMSO-d6): δ 3.98 (s, 2H), 6.93 (d of t, 1H), 7.38 (d of d, 1H), 7.44 (d of d, 1H), 7.50 (d, 1H), 7.77–7.80 (m, 2H), 11.72 (s, 1H), 13.43 (s, 1H); MS [EI, m/z]: 267 [M]+.

Elemental analysis for $C_{16}H_{10}FNO_2$

Calc'd: C, 71.91; H, 3.77; N, 5.24

Found: C, 71.33; H, 3.78; N, 5.22

EXAMPLE 20

8-Chloro-5,10-dihydro-indeno[1,2-b]indole-1-carboxylic acid

In a manner similar to Example 17, 1-oxo-indan-4-carboxylic acid (1.00 g, 5.68 mmol) and 4-chlorophenylhydrazine hydrochloride (1.03 g, 5.75 mmol) were converted to the title compound (0.230 g, 14%) as a pale brown solid: mp>300° C.; $^1$H NMR (DMSO-d6,): δ 4.00 (s, 2H), 7.10 (d of d, 1H), 7.46 (d, 1H), 7.51 ( d, 1H), 7.66 (d, 1H), 7.78–7.81 (m, 2H), 11.83 (s, 1H), 13.57 (s, 1H); MS [EI, m/z]: 283 [M]$^+$.

Elemental analysis for $C_{16}H_{10}ClNO_2$

Calc'd: C, 67.74; H, 3.55; N, 4.94

Found: C, 67.08; H, 3.69; N, 4.78

EXAMPLE 21

8-Trifluoromethoxy-5,10-dihydro-indeno[1,2-b]indole-1-carboxylic acid

In a manner similar to Example 17, 1-oxo-indan-4-carboxylic acid (1.00 g, 5.68 mmol) and 4-trifluoromethoxyphenylhydrazine hydrochloride (1.30 g, 5.68 mmol) were converted to the title compound (0.160 g, 8%) as an light tan solid: mp 256–265 (dec)° C.; $^1$H NMR (DMSO-d6): δ 4.03 (s, 2H), 7.05–7.08 (m, 1H), 7.49 (d, 1H), 7.53 (d, 1H), 7.61 (d, 1H), 7,79–7.83 (m, 2H), 11.92 (s, 1H), 13.08 (s, 1H); MS [EI, m/z]: 333 [M]$^+$.

Elemental analysis for $C_{17}H_{10}F_3NO_3$

Calc'd: C, 61.27; H, 3.02; N, 4.20

Found: C, 60.82; H, 3.15; N, 4.32

EXAMPLE 22

8-Chloro-5,10-dihydro-indeno[1,2-b]indole-1-carboxylic acid ethyl ester

The product of Example 20 was converted to its ethyl ester by treatment with sulfuric acid in ethanol to give the title compound as an off-white solid: mp 202–204° C.; $^1$H NMR (DMSO-d6,): δ 1.39 (t, 3H), 4.00 (s, 2H), 4.38 (q, 2H), 7.11 (d, 1H), 7.48 (d, 1H), 7.52 (t, 1H), 7.67 (s, 1H), 7.79–7.84 (m, 2H), 11.86 (s, 1H); MS [EI, m/z]: 311 [M]$^+$.

Elemental analysis for $C_{18}H_{14}ClNO_2$

Calc'd: C, 60.69; H, 3.96; N, 3.93

Found: C, 60.47; H, 3.76; N, 3.78

EXAMPLE 23

8-Bromo-5,10-dihydro-indeno[1,2-b]indole-1-carboxylic acid ethyl ester

In a manner similar to Example 17, 1-oxo-indan4-carboxylic acid and 4-bromophenylhydrazine hydrochloride were reacted to form 8-bromo-5,10-dihydro-indeno[1,2-b]indole-1-carboxylic acid which was converted to the ethyl ester in a manner similar to that described in Example 22 to afford the title compound as a tan solid: mp 198–200° C.; $^1$H NMR (DMSO-d6): δ 1.39 (t, 3H), 4.00 (s, 2H), 4.37 (q, 2H), 7.22 (d, 1H), 7.42 (d, 1H), 7.52 (t, 1H), 7.79–7.84 (m, 3H), 11.86 (s, 1H); MS [EI, m/z]: 355 [M]$^+$.

Elemental analysis for $C_{18}H_{14}BrNO_2$

Calc'd: C, 69.35; H, 4.53; N, 4.49

Found: C, 69.17; H, 4.39; N, 4.37

EXAMPLE 24

10,10-Dimethyl-3-nitro-5,10-dihydro-indeno[1,2-b]indole-6-carboxylic acid

6-Nitro-3,3-dimethyl-1-indanone (0.612 g, 2.98 mmol) [Smith, J. G. et al. *Org. Prep. and Proc. Int.* 1978, 10(3), 123–131] and 2-hydrazinobenzoic acid hydrochloride (0.562 g, 2.98 mmol) in formic acid (2 mL, 96%) were irradiated for two minutes in a closed cap Teflon vessel of a microwave oven (700 W). The mixture was vacuum filtered, and the crude product was chromatographed (hexane/ethyl acetate 1:1) and triturated with petroleum ether/diethyl ether. Drying in vacuo afforded 0.178 g (19%) of the title compound as a yellow solid: mp 310° C. (dec); $^1$H NMR (DMSO-d6): δ 13.43 (s, 1H), 11.85 (s, 1H), 8.95 (s, 1H), 8.12 (d, 1H), 7.98 (d, 1H), 7.81 (m, 2H), 7.19 (t, 1H), 1.59 (s, 6H); IR (KBr): 3460, 1670 cm$^{-1}$; MS (m/z) 322 (M$^+$).

Elemental analysis for $C_{18}H_{14}N_2O_4$

Calc'd: C, 67.08; H, 4.38; N, 8.69.

Found: C, 66.29; H, 4.45; N, 8.37.

EXAMPLE 25

8-Bromo-5,10-dihydro-indeno[1,2-b]indole-1-carboxylic acid

1-Oxo-4-indancarboxylic acid (0.528 g, 2.98 mmol) [Aono, T. et al., *Chem. Pharm. Bull.* 1978,26(4)1153–1161] and 2-hydrazinobenzoic acid hydrochloride (0.566 g, 2.98 mmol) in formic acid (2 mL, 96%) were irradiated for two minutes in a closed cap Teflon vessel of a microwave oven (700 W). The mixture was vacuum filtered. The crude product was dissolved in acetone/diethyl ether (1:1) and treated with decolorizing carbon, filtered, concentrated and dried in vacuo to yield 0.530 g (54%) of title compound as a white solid: mp 328–330° C. (dec); $^1$H NMR (DMSO-d6): δ 13.43 (s, 1H), 11.85 (s, 1H), 7.78–7.83 (m, 3H), 7.50 (t, 1H), 7.43 (d, 1H), 7.21 (d, 1H), 4.00 (s, 2H); IR (KBr): 3440, 1690 cm$^{-1}$; MS (m/z) 327 (M$^+$).

Elemental analysis for $C_{16}H_{10}BrNO_2$

Calc'd: C, 58.56; H, 3.07; N, 4.27.

Found: C, 58.57; H, 2.88; N, 4.30.

EXAMPLE 26

3-Bromo-5,10-dihydro-indeno[1,2-b]indole-6-carboxylic acid

Step 1) Preparation of o-[(2,3-dihydro-6-bromoinden-3-ylidene)hydrazino]-benzoic acid To a solution of 6-bromoindanone (0.447 g, 2.12 mmol) [Adamczyk, M. et al. *J. Org. Chem.* 1984, 49, 4226–4237] in ethanol (100 mL) was added a solution of 2-hydrazinobenzoic acid hydrochloride (0.800 g, 4.24 mmol) in deionized water (50 mL). The mixture was stirred for 1 h then cooled to 0° C. The precipitated hydrazone was vacuum filtered and dried in vacuo to afford 0.628 g (86%) of the title compound as a yellow solid: mp 186° C. (dec).

Step 2) Preparation of 3-Bromo-5,10-dihydro-indeno[1,2-b]indole-6-carboxylic acid The hydrazone (from Step 1, Example 26 above) (0.620 g, 1.80 mmol) in formic acid (2 mL, 96%) was irradiated for two minutes in a microwave oven (700 W) in a closed cap Teflon vessel. The reaction mixture was vacuum filtered hot and the solid was dried in vacuo to yield 0.360 g (61%) of the title compound as a yellow solid: mp 245–247° C. (dec); $^1$H NMR (DMSO-d6): δ 13.43 (s, 1H), 11.73 (s, 1H), 8.32 (s, 1H), 7.86 (d, 1H), 7.78 (d, 1H), 7.49 (d, 1H), 7.36 (d, 1H), 7.16 (t, 1H), 3.71 (s, 2H); IR (KBr): 3460, 1650 cm$^{-1}$; MS (m/z) 327 (M$^+$).

Elemental analysis for $C_{16}H_{10}BrNO_2$

Calc'd: C, 58.56; H, 3.07; N, 4.27.

Found: C, 58.62; H, 2.83; N, 4.22.

Examples 27–32 Are Prepared In a Manner Similar to That Described for Example 17 Using The Appropriate Phenyl Hydrazine and 1-Oxo-indan-4-carboxylic acid

EXAMPLE 27

8-Bromo-7-methoxy-5,10-dihydro-indeno[1,2-b]indole-1-carboxylic acid

EXAMPLE 28

8-Bromo-6-methoxy-5,10-dihydro-indeno[1,2-b]indole-1-carboxylic acid

EXAMPLE 29

8-Chloro-7-methoxy-5,10-dihydro-indeno[1,2-b]indole-1-carboxylic acid

EXAMPLE 30

8-Chloro-6-methoxy-5,10-dihydro-indeno[1,2-b]indole-1-carboxylic acid

EXAMPLE 31

8-Bromo-9-methoxy-5,10-dihydro-indeno[1,2-b]indole-1-carboxylic acid

EXAMPLE 32

8-Bromo-6-methoxy-5,10-dihydro-indeno[1,2-b]indole-1-carboxylic acid

Examples 33–36 Are Prepared In a Manner Similar to That Described for Example 1 Using The Appropriate Benzofuranone and 2-Hydrazinobenzoic Acid

EXAMPLE 33

8-Bromo-7-methoxy-10H-benzo[4,5]furo[3,2-b]indole-1-carboxylic acid

EXAMPLE 34

8-Chloro-7-methoxy-10H-benzo[4,5]furo[3,2-b]indole-1-carboxylic acid

EXAMPLE 35

8-Chloro-9-methoxy-10H-benzo[4,5]furo[3,2-b]indole-1-carboxylic acid

EXAMPLE 36

8-Chloro-6-methoxy-10H-benzo[4,5]furo[3,2-b]indole-1-carboxylic acid

The smooth muscle (bladder) relaxing activity of the compounds of this invention was established in accordance with standard pharmaceutically accepted test procedures with representative compounds as follows.

Sprague-Dawley rats (150–200 g) are rendered unconscious by $CO_2$ asphyxiation and then euthanized by cervical dislocation. The bladder is removed into warm (37° C.) physiological salt solution (PSS) of the following composition (mM): NaCl, 118.4; KCl, 4.7; $CaCl_2$, 2.5; $MgSO_4$, 4.7; $H_2O$, 1.2; $NaHCO_3$, 24.9; $KH_2PO_4$, 1.2; glucose, 11.1; EDTA, 0.023; gassed with 95% $O_2$; 2/5% $CO_2$; pH 7.4. The bladder is opened and then cut into strips 1–2 mm in width and 7–10 mm in length. The strips are subsequently suspended in a 10 mL tissue bath under an initial resting tension of 1.5 g. The strips are held in place by two surgical clips one of which is attached to a fixed hook while the other is attached to an isometric force transducer. The preparations, which usually exhibit small spontaneous contractions, are allowed to recover for a period of 1 hour prior to a challenge with 0.1 μM carbachol. The carbachol is then washed out and the tissue allowed to relax to its resting level of activity. Following a further 30 min period of recovery an additional 15 mM KCl are introduced into the tissue bath. This increase in KCl concentration results in a large increase in the amplitude of spontaneous contractions (and initiation of contractions in previously quiescent strips) superimposed upon a small increase in basal tone. Following stabilization of this enhanced level of contractile activity, incremental increases in the concentration of test compound or vehicle are introduced into the tissue bath. Contractile activity is measured for each compound or vehicle concentration during the last minute of a 30 minute challenge.

The isometric force developed by the bladder strips is measured using a concentration required to elicit 50% inhibition of pre-drug contractile activity ($IC_{50}$ concentration) and is calculated from this concentration-response curve. The maximum percentage inhibition of contractile activity evoked by a test compound is also recorded for concentrations of test compound less than or equal to 30 μM.

The smooth muscle (aorta) relaxing activity of the compounds of this invention was established in accordance with standard pharmaceutically accepted test procedures with representative compounds as follows.

Male Sprague-Dawley rats (150–200 g) are rendered unconscious by $CO_2$ asphyxiation and then euthanized by cervical dislocation. The thoracic aorta is removed into warm (37° C.) physiological salt solution (PSS) of the following composition (mM): NaCl, 118.4; KCl, 4.7; $CaCl_2$, 2.5; $MgSO_4.7H_2O$, 1.2; $NaHCO_3$, 24.9; $KH_2PO_4$, 1.2; glucose, 11.1; EDTA, 0.023; gassed with 95% $O_2$/5% $CO_2$; pH 7.4. The aorta is cleaned of fat and loose adventitia and cut into rings 3–4 mm in width. The rings are subsequently suspended between two stainless steel wire tissue holders in a 10 mL tissue bath. One wire tissue holder is attached to a fixed hook while the other is attached to an isometric force transducer. Resting tension is set at 1 g. The tissues are to recover for a period of 60 min prior to beginning the experiment. Tissues are challenged with PSS containing 25 mM KCl to elicit a contracture. The tissues are then washed repeatedly with fresh PSS over a period of 30 min and allowed to recover to baseline tension. PSS containing 30–35 mM KCl is then introduced into the tissue bath to evoke a contracture that is allowed to stabilize for not less than 45 min. (Other stimuli such as norepinephrine, PGF2a, histamine, angiotensin II, endothelin or PSS containing 80 mM KCl may also be used to evoke a contracture as necessary). Increasing concentrations of test compound or vehicle are then added to the tissue bath in a cumulative fashion.

Isometric force development by the aortic rings is measured using a force transducer and recorded on a polygraph. The percentage inhibition of contractile force evoked by each concentration of a given test compound is used to generate a concentration-response curve. The concentration of test compound required to elicit 50% inhibition of pre-drug contractile force ($IC_{50}$ concentration) is calculated from this dose-response curve. [Log concentration versus response curves are approximately linear between 20% and 80% of the maximum response. As such, the $IC_{50}$ concentration of the drug is determined by linear regression analysis (where x=log concentration and y=% inhibition) of the data points in the 20% to 80% region of the curve.] The maximum percentage inhibition of contractile force evoked by a test compound is also recorded for concentrations of test compound <or=to 30 uM. Data collected from 2 animals are averaged for primary screens.

The results of these studies are shown in Table I.

| Example Number | n | Bladder Tissue $IC_{50}$ ($\mu$M) | n | Aorta Tissue $IC_{50}$ ($\mu$M) | Ratio Aorta $IC_{50}$ Bladder $IC_{50}$ |
|---|---|---|---|---|---|
| 1 | 8 | 15.1 ± 4.7 | 4 | 118.8 ± 21.8 | 79 |
| 2 | 8 | 6.1 ± 3.0 | 3 | 128 ± 16.9 | 21 |
| 3 | 6 | 5.8 ± 1.5 | 4 | 268.0 ± 82.3 | 46.2 |
| 4 | 8 | 6.3 ± 2.6 | 3 | 125 ± 13.8 | 19.8 |
| 5 | 2 | I = 13.5%* | | | — |
| 6 | 4 | I = 31%* | | | — |
| 8 | 3 | 19.8 ± 4.02 | 3 | 8.1 ± 3.6 | 0.41 |
| 9 | 2 | I = 19%* | | | — |
| 10 | 4 | I = 10.1%* | | | — |
| 11 | 2 | I = 30.9%* | | | — |
| 12 | 2 | 13.9 ± 0.95 | 3 | 25 ± 3.9 | 1.8 |
| 13 | 2 | I = 28.5%* | | | — |
| 14 | 3 | I = 4.8%* | | | — |
| 15 | 2 | I = 4.5%* | | | — |
| 16 | 4 | 31.0 ± 6.5 | | | — |
| 17 | 8 | 10.1 ± 3.2 | | | — |
| 18 | 2 | I = 5.2%* | | | — |
| 19 | 6 | 12.5 ± 5 | 3 | 46.6 ± 18.7 | 3.74 |
| 20 | 5 | 22.6 ± 1.8 | | | — |
| 21 | 4 | 15.4 ± 4.8 | | | — |
| 22 | 2 | I = 8%* | | | — |
| 23 | 2 | I = 20%* | | | — |
| 24** | 4 | 5.2 ± 1.8 | 4 | 17.2 ± 2.3 | 3.3 |
| 25 | 8 | 4.4 ± 0.95 | 6 | 109.6 ± 12.4 | 25 |
| 26 | 7 | 8.6 ± 3.0 | 4 | 210.4 ± 45 | 24.5 |

* Percent inhibition at 30 $\mu$M

Several compounds in this invention were tested for their ability to relax a whole rat bladder ex-vivo. The protocol for this assay is as follows.

Female Spraque-Dawley rats weighing between 200–300 g were anesthetized with NEMBUTOL® (50 mg/kg, i.p.). After achieving adequate anesthesia, the bladder and urethra were exposed through a mid-line incision. A 4-0 silk ligature was tied around the proximal end of the urethra in the presence of a 1 mm diameter stainless steel rod. The rod was then removed resulting in a partial outlet obstruction. The wound was closed with surgical staples and the animals received 15,000 units of BICILLIN® antibiotic. After a 6 week period the animals were asphyxiated with $CO_2$ gas. Bladders for contractile analysis were placed in a physiological salt solution (PSS) at 37° C. of the following composition (in mM): NaCl (118.4), KCl (4.7), $CaCl_2$ (2.5), $MgSO_4$ (1.2), $KH_2PO_4$ (1.2), $NaHCO_3$ (24.9) and D-glucose (11.1) gassed with $CO_2$-$O_2$ (95%–5%) to achieve a pH of 7.4.

The isolated bladders were secured through the urethral opening with a silk ligature to a length of polyethylene tubing (PE-200). The opposite end of the tubing was connected to a pressure transducer to monitor developed bladder pressure. The bladders were placed in a tissue bath containing PSS at 37° C. and inflated with PSS to achieve optimal contractions. Bladder contractions were displayed and monitored on a Grass model 7D polygraph.

Following stabilization, incremental increases in the concentration of test compound or vehicle are introduced into the tissue bath. Contractile activity is measured for each compound or vehicle concentration during the last minute of a 30 minute challenge. Concentration required to elicit 50% inhibition of pre-drug contractile activity ($IC_{50}$ concentration) is calculated from this concentration-response curve. The maximum percentage inhibition of contractile activity evoked by a test compound is also recorded for concentrations of test compound less than or equal to 30 $\mu$M. Example 24 exhibited an $IC_{50}$ value of 5 $\mu$M in this assay.

Based on the results of the standard pharmacological test procedures, the compounds of this invention are selective for bladder tissue and have a pronounced effect on smooth muscle contractility and are useful in the treatment of urinary incontinence, irritable bladder and bowel disease, asthma, stroke, and similar diseases as mentioned above, which are amenable to treatment with potassium channel activating compounds by administration, orally, parenterally, or by aspiration to a patient in need thereof.

We claim:

1. A compound of the general Formula (I):

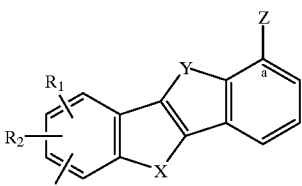

(I)

wherein:

$R_1$, $R_2$ and $R_3$ are, independently, hydrogen, halogen, nitro, cyano, alkyl of 1 to 10 carbon atoms, cycloalkyl of 3 to 10 carbon atoms, alkoxy of 1 to 10 carbon atoms (optionally substituted with halogen), amino, alkylamino of 1 to 10 carbon atoms, —$SO_3H$, —$SO_2NH_2$, —$NHSO_2R_{14}$,

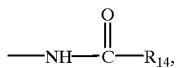

$R_{15}SO_2$-, carboxyl and aryl of 6 to 12 carbon atoms, or an acyl substituent selected from formyl, alkanoyl of 2 to 7 carbon atoms, alkenoyl of 3 to 7 carbon atoms, alkylsulfonyl of 1 to 7 carbon atoms, aroyl of 7 to 12 carbon atoms, arylalkenoyl of 9 to 20 carbon atoms, arylsulfonyl of 6 to 12 carbon atoms, arylalkanoyl of 8 to 12 carbon atoms or arylalkylsulfonyl of 7 to 12 carbon atoms;

Y is —O— or —$NR_4$;

X is —O—, when Y is —$NR_4$;

X is —$NR_4$, when Y is —O—;

$R_4$ is hydrogen, alkyl of 1 to 10 carbon atoms, cycloalkyl of 3 to 10 carbon atoms, aryl of 6 to 12 carbon atoms, or an acyl substituent selected from formyl, alkanoyl of 2 to 7 carbon atoms, alkenoyl of 3 to 7 carbon atoms, alkylsulfonyl of 1 to 7 carbon atoms, aroyl of 7 to 12 carbon atoms, arylalkenoyl of 9 to 20 carbon atoms, arylsulfonyl of 6 to 12 carbon atoms, arylalkanoyl of 8 to 12 carbon atoms and arylalkylsulfonyl of 7 to 12 carbon atoms;

Z substituted at position a is selected from the group consisting of

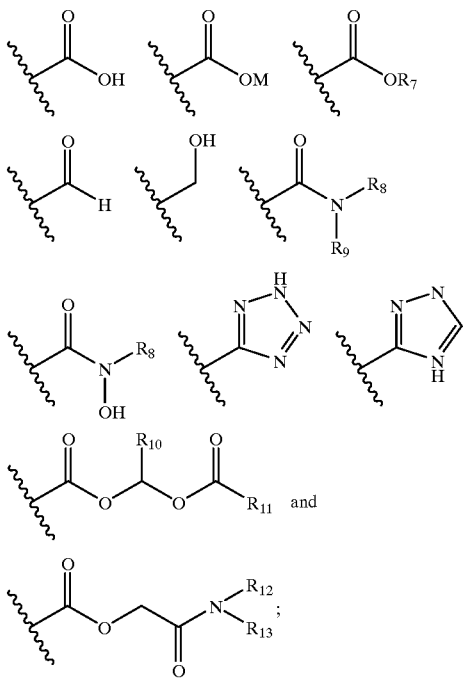

M is an alkali metal cation or an alkaline earth metal cation;
$R_7$ is alkyl of 1 to 10 carbon atoms, cycloalkyl of 3 to 10 carbon atoms, aralkyl of 7 to 20 carbon atoms, or aryl of 6 to 12 carbon atoms;
$R_8$ and $R_9$ are, independently, hydrogen, alkyl of 1 to 10 carbon atoms, cycloalkyl of 3 to 10 carbon atoms, aralkyl of 7 to 20 carbon atoms, or aryl of 6 to 12 carbon atoms;
$R_{10}$, $R_{11}$, $R_{12}$ and $R_{13}$ are independently, alkyl of 1 to 10 carbon atoms;
$R_{14}$ is a straight chain alkyl of 1 to 10 carbon atoms;
$R_{15}$ is a straight chain alkyl of 1 to 10 carbon atoms (optionally substituted with halogen);
aroyl is —C(O)aryl;
aryl is a homocyclic aromatic radical, whether or not fused having 6 to 12 carbon atoms optionally substituted with one to three substituents each independently selected from the group halogen, carboxy, alkyl of 1 to 10 carbon atoms, nitro, amino, alkoxy of 1 to 10 carbon atoms, and alkylamino of 1 to 10 carbon atoms;
provided that $R_1$, $R_2$ and $R_3$ are not hydrogen when Z is —CHO, Y is —O— and X is —N—CH$_3$;
or a pharmaceutically acceptable salt thereof.

2. A compound of claim 1 wherein X is —O— when Y is —NR$_4$ or a pharmaceutically acceptable salt thereof.

3. A compound of claim 1 wherein X is —O— when Y is —NR$_4$ and $R_1$ is halogen or nitro and Z is —CO$_2$H or a pharmaceutically acceptable salt thereof.

4. A compound of claim 1 wherein X is —NR$_4$ when Y is —O— and $R_1$ is halogen or nitro and Z is —CO$_2$H or a pharmaceutically acceptable salt thereof.

5. The compound according to claim 1 which is selected from the group consisting of:
8-Bromo-10H-benzo[4,5]furo[3,2-b]indole-1-carboxylic acid;
8-Iodo-10H-benzo[4,5]furo[3,2-b]indole-1-carboxylic acid;
8-Chloro-10H-benzo[4,5]furo[3,2-b]indole-1-carboxylic acid;
8-Nitro-10H-benzo[4,5]furo[3,2-b]indole-1-carboxylic acid dihydrate;
8-Bromo-10H-benzo[4,5]furo[3,2-b]indole-1-carboxylic acid amide;
8-Bromo-10H-benzo[4,5]furo[3,2-b]indole-1-carboxylic acid methyl ester;
(8-Bromo-10H-benzo[4,5]furo[3,2-b]indole-1-yl)-methanol;
8-Bromo-10H-benzo[4,5]furo[3,2-b]indole-1-carboxylic acid hydroxy-methyl amide;
8-Bromo-10H-benzo[4,5]furo[3,2-b]indole-1carbaldehyde;
8-Bromo-1-(1H-tetrazol-5-yl)-10H-benzo[4,5]furo[3,2-b]indole;
8-Bromo-10H-benzo[4,5]furo[3,2-b]indole-1-carboxylic acid (1,2,2-trimethyl-propyl)-amide;
8-Bromo-10H-benzo[4,5]furo[3,2-b]indole-1-carboxylic acid (1,1-dimethyl-propyl)-amide;
8-Bromo-10H-benzo[4,5]furo[3,2-b]indole-1-carboxylic acid methylamide;
8-Bromo-10-methyl-10H-benzo[4,5]furo[3,2-b]indole-1-carboxylic acid methyl ester; and
10H-Benzo[4,5]furo[3,2-b]indole-1-carboxylic acid;
or a pharmaceutically acceptable salt thereof.

6. A pharmaceutical composition for treating or inhibiting disorders associated with smooth muscle contraction, via potassium channel modulation in warm-blooded animals in need thereof, which comprises administering to said warm-blooded animals, an effective amount of a compound of claim 1 or a pharmaceutically acceptable salt thereof and one or more pharmaceutically acceptable carriers or excipients.

7. A pharmaceutical composition according to claim 6 wherein X is —O— when Y is —NR$_4$ or a pharmaceutically acceptable salt thereof.

8. A pharmaceutical composition according to claim 6 wherein X is —O— when Y is —NR$_4$ and $R_1$ is halogen or nitro and Z is —CO$_2$H or a pharmaceutically acceptable salt thereof.

9. A pharmaceutical composition according to claim 6 wherein X is —NR$_4$ when Y is —O— and $R_1$ is halogen or nitro and Z is —CO$_2$H or a pharmaceutically acceptable salt thereof.

10. A method of treating or inhibiting disorders associated with smooth muscle contraction, via potassium channel modulation in warm-blooded animals in need thereof, which comprises administering to said warm-blooded animals, an effective amount of a compound of claim 1 or a pharmaceutically acceptable salt thereof.

11. A method according to claim 10 wherein X is —O— when Y is —NR$_4$ or a pharmaceutically acceptable salt thereof.

12. A method according to claim 10 wherein X is —O— when Y is —NR$_4$ and $R_1$ is halogen or nitro and Z is —CO$_2$H or a pharmaceutically acceptable salt thereof.

13. A method of claim 10 in which the smooth muscle adversely contracting causes urinary incontinence.

14. A method of claim 10 in which the smooth muscle adversely contracting causes irritable bowel syndrome.

15. A method according to claim 10 wherein X is —NR$_4$ when Y is —O— and $R_1$ is halogen or nitro and Z is —CO$_2$H or a pharmaceutically acceptable salt thereof.

16. A compound of claim 1 wherein X is —O— when Y is —NR$_4$ and $R_1$ is halogen and Z is —CO$_2$H or a pharmaceutically acceptable salt thereof.

17. A compound according to claim 1 wherein X is —NR$_4$ when Y is —O—and $R_1$ is halogen and Z is —CO$_2$H or a pharmaceutically acceptable salt thereof.

18. A pharmaceutical composition according to claim 6 wherein X is —NR$_4$ when Y is —O— and $R_1$ is halogen and Z is —CO$_2$H or a pharmaceutically acceptable salt thereof.

19. A method according to claim 10 wherein X is —NR$_4$ when Y is —O— and $R_1$ is halogen and Z is —CO$_2$H or a pharmaceutically acceptable salt thereof.

* * * * *